United States Patent [19]

Lindstrom et al.

[11] Patent Number: 4,696,917

[45] Date of Patent: Sep. 29, 1987

[54] IRRIGATION SOLUTION

[76] Inventors: Richard L. Lindstrom, 1065 W. Ferndale Rd., Wayzata, Minn. 55391; Debra L. Skelnik, Box 344, Rte. 5, Cambridge, Minn. 55008

[21] Appl. No.: 761,407

[22] Filed: Aug. 1, 1985

[51] Int. Cl.$^4$ .............................................. A61K 31/70
[52] U.S. Cl. ........................................ 514/54; 514/23
[58] Field of Search ................................. 514/54, 23

[56] References Cited

PUBLICATIONS

Kaufman et al., *American Journal of Ophthalmology,* 1984, pp. 112–114.

Lindstrom et al., *Chemical Abstracts,* vol. 103, 1985, No. 156864r.

*Primary Examiner*—Johnnie R. Brown
*Assistant Examiner*—Elli Peselel
*Attorney, Agent, or Firm*—Hugh D. Jaeger

[57] ABSTRACT

An irrigation solution which provides the anterior and posterior chamber of the eye protection during surgical procedures that require irrigation. This irrigation solution is composed of a HEPES buffered Eagle's Minimum Essential Media (MEM) with Earle's Salts, without phenol red, supplemented with mixed isomers of 99% pure, chondroitin sulfate, MEM non-essential amino acids, 2-mercaptoethanol, and sodium pyruvate.

6 Claims, No Drawings

IRRIGATION SOLUTION

BACKGROUND OF THE INVENTION

1. Field of the Invention

The present invention pertains to an intraocular irrigation solution for the anterior and posterior chamber of the eye.

2. Description of the Prior Art

There are two intraocular irrigation solutions presently being two intraocular irrigation solutions presently being used in ophthalmic surgeries. These two irrigation solutions are BSS and BSS Plus. BSS is a balanced salt solution that incorporates a sodium citrate of a balanced salt solution with a bicarbonate buffering system, with Dextrose added as an additional osmotic agent and energy source. An additional component, oxidized glutathione is reduced by the ocular cells and serves as an anti-oxidant.

SUMMARY OF THE INVENTION

This irrigation solution provides the anterior and posterior chamber of the eye protection during surgical procedures that require irrigation. This irrigation solution specifically protects corneal endothelium in anterior segment surgery. The corneal endothelium and other anterior and posterior chamber structures will be in direct contact with this irrigation solution. This intraocular irrigation solution includes: 1. A protective coating agent, chondroitin sulfate, a highly negatively charged glycosaminoglycan. Chondroitin sulfate is a naturally occurring, biodegradable material normally found in the human cornea. 2. An effective reducing agent, 2-mercaptoethanol, that can be utilized in both the oxidized and reduced forms by human corneal endothelial cells. 3. An additional buffering agent HEPES (N'-2-hydroxyethylpiperazine-N'-Ethanesulfonic Acid). HEPES buffer tends to stabilize and resist rapid changes in pH in mdeia solutions. The HEPES component will provide a more stable pH for this irrigation solution. Bicarbonate is also found in this irrigation solution, as a necessary buffering component required by ocular cells. 4. An additional substrate, sodium pyruvate, is provided for additional biosynthetic syntheses that may be required by the ocular cells after surgical trauma. 5. The base media of this irrigation solution cosists of Eagle's Minimum Essential Media (MEM) supplemented with 1% MEM non-essential amino acids, which is nutritionally complete for ocular cells.

This irrigation solution is designed to protect the anterior segment of the cornea during surgical procedures, to maintain in homeostasis after surgical trauma, and to provide necessary metabolic substrates that may be needed for wound repair. A completely defined media Eagle's Minimum Essential media with Earle's salts, without phenol red, is supplemented with a protective agent, chodroitin sulfate; a reducing agent, 2-mercaptoethanol; an alternative energy source, sodium pyruvate; and an additional buffering agent, HEPES; to make a more effective and stable irrigation solution for use in ophthalmic surgeries.

DESCRIPTION OF THE PREFERRED EMBODIMENTS

Eagle's Minimum Essential Media with Eare's salts without L-glutamine, and without phenol red (GIBCO), supplemented with 15 mM HEPES BUFFER, 0.40% chondroitin sulfate, mixed isomers 99.9% pure (SIGMA) with 0.5 mM 2-mercaptoethanol, 1 mM sodium pyruvate and 0.1 mM MEM non-essential amino acids.

RANGES: The chondroitin sulfate can be in a range of 0.1% to 5%. The 2-mercaptoethanol can be in a range of 0.001 mM to 1 mM. The HEPES buffer can be in a range of 5 mM to 30 mM. The sodium pyruvate at a range of 0.05 mM to 2 mM and MEM non-essential amino acids at 0.05 mM to 0.2 mM.

Additionally, the following compounds can be added as so desired:

1. Ascorbic acid in a range of 0.01–0.2 mM, preferred 0.1 mM;
2. Glutathione in a range of 0.1 ug/ml–5mg/ml, preferred 0.3 mM;
3. DL-α-Tocopherol (Vitamin E) in a range of 0.001 ug/ml–0.1 ug/ml, preferred, 0.01 ug/ml;
4. FGF (Fibroblastic Growth Factor) by Collaborative Research, Inc., in a range of 1 ng/ml–10 ug/ml, preferred 10 ng/ml;
5. ECGF (Endothelial Cell Growth Factor) in a range of 200 ng/ml–500 ug/ml, preferred 300 ug/ml; or,
6. Sialic acid in a range of 1 mM–0.001 mM, preferred 0.11 mM.

The base of this intraocular irrigation solution is a completely defined media, supplemented with MEM non-essential amino acids. This replaces the prior art of using a balanced salt solution found in both BSS and BBS Plus.

The exposure time to the irrigation solution in normal ophthalmic surgical procedures is normally 3 to 8 minutes, a very limited time period. But upon special occasions, the anterior chamber is filled with the irrigation solution and allowed to remain there until the aqueous humor is remade, which may take up to 24 hours. During this time, the anterior chamber cells are deprived of necessary nutrients, normally supplied by the aqueous humor. Although the anterior segment cells, most significantly the corneal endothelium, are supplied with nutrients from their basal side, most of the metabolic uptake is from the anterior side, most of the metabolic uptake is from the anterior surface. The corneal endothelium maintains the clarity of the cornea by actively pumping salts and water out of conective tissue stroma into the anterior chamber of the eye. The $Na^+$- $K^+$-ATPase pump of the endothelial cells requires ATP and reduced pump sites to keep this pump functional. When the pumping action of these corneal endothelial cells is reduced, the cornea imbibes fluids and becomes thickened and looses optical clarity. Therefore, an irrigation solution with a reducing agent is of considerable advantage. One of the major disadvantages of BSS Plus, with the reducing agent glutathione and the bicarbonate buffering system, is the lack of stability of the solution once prepared. The glutathione component of the irrigation solution is added separately to the solution, and the solution is stable for only a 24 hour period. The buffering ability of the bicarbonate in this irrigation solution is greatly reduced once the solution is exposed to the atmosphere.

The irrigation solution of the present invention effectively deals with these two problems by the addition of 2-mercaptoethanol and an additional HEPES buffering system. 2-mercaptoethanol is an effective reducing agent that can be utilized by human corneal endothelial cells. The HEPES buffering system, in addition to the necessary bicarbonate buffering system, resists rapid changes in the pH of the irrigation solution that may occur with bicarbonate alone. The addition of these two components provides the stable irrigation solution.

EXAMPLE 1

Eagle's Minimum Essential Media with Earle's salts without L-glutamine and phenol red, with:
0.1% to 5% chondroitin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids.

EXAMPLE 2

Eagle's Minimum Essential Media with Earle's salts without L-glutamine and phenol red, with:
0.1% to 5% chondroitin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids,
0.01 mM to 0.2 mM ascorbic acid.

EXAMPLE 3

Eagle's Minimum Essential Media with Earle's salts without L-glutamine and phenol red, with:
0.1% to 5% chondroitin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids,
0.1 ug/ml to 5 mg/ml glutathione.

EXAMPLE 4

Eagle's Minimum Essential Media with Earle's salts without L-glutamine and phenol red, with:
0.1% to 5% chondroitin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids,
0.001 ug/ml to 0.1 ug/ml DL-Tocopherol.

EXAMPLE 5

Eagle's Minimum Essential Media with Earle's salts without L-glutamine and phenol red, with:
0.1% to 5% chondroitin sulfate (99.95 pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids
0.1 ng/ml to 10 ug/ml FGF (Fibroblastic Growth Factor from Collaborative Research, Inc.).

EXAMPLE 6

Eagle's Minimum Essential Media with Earle's salts without L-glutamine and phenol red, with:
0.1% to 5% chondrotin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids,
200 ng/ml to 500 ng/ml ECGF (Endothelial Cell Growth Factor from Collaborative Research, Inc.)

EXAMPLE 7

Eagle's Minimum Essential Media with Earle's salts without L-glutamine and phenol red, with:
0.1% to 5% chondroitin sulfate (99.9% pure mixed isomers (SIGMA)) 5 mM to 30 mM HEPES buffer,
0.001 mM to 1 mM 2-mercaptoethanol,
0.05 mM to 2 mM sodium pyruvate,
0.05 mM to 0.2 mM MEM non-essential amino acids,
0.001 to 1 mM sialic acid.

Three additional components have been added to the irrigation solution to increase its effectiveness in protecting and repairing the anterior segment of the cornea during and after surgical trauma. Chondroitin sulfate, a highly negatively charged glycosamioglycan is added to replace any glycosaminoglycan that may be removed from the surface of the corneal andothelial cells from the disruption of aqueous flow or surgical trauma. Glycosaminoglycans are necessary for membrane stability and the maintenance of the three-dimensional structure of receptor proteins. These receptor proteins are required for the metabolic processes of the cell. Chondrotin sulfate acts as a protective coating for the anterior segment cells. An additional substrate, sodium pyruvate, is provided for additional biosynthetic synthesis that may be required by these anterior segment cells after surgical trauma. The third component, MEM non-essential amino acids, are added to supplement the irrigation solution to provide additional amino acids that may be required for wound repair after surgical trauma.

Significant uses of this irrigation solution include: 1. As an ophthalmic irrigating and lubricating eye drop. 2. In the irrigation of burn wounds. 3. As a general irrigation solution for use in surgeries where irrigation is required.

Specific applications in the use of this irrigation solution include: 1. The flushing of ova, and embryos from human and non-human animals in embryo and ova transfer techniques. 2. In vitro fertilization procedures, which includes maintenance of sperm and ova during this procedure. 3. In vitro maintenance of immature and mature ova and embryos. 4. Transfer of ova and embryos back into the recipient uterus.

What is claimed is:

1. A composition for the irrigation and flushing of body tissue during surgical procedures, which composition comprises effective amounts of:
   a. Eagle's Minimum Essential Medium with Earle's salts, without L-glutamine and phenol red, and supplemented with non-essential amino acids;
   b. chondroitin sulfate;
   c. a buffer system based on N'-2-hydroxyethylpiperazine-N'ethane sulfonic acid;
   d. 2-mercaptoethanol; and,
   e. a pyruvate.

2. The composition of claim 1 in which component (b) is present at a concentration of about 0.1–5% by weight, and components (c), (d) and (e) are present at concentrations of about 5–30 mM, 0.001–1 mM and 0.05–2 mM, respectively.

3. The composition of claim 1 additionally containing at least one of:
   a. ascorbic acid;
   b. glutathione;
   c. DL-L-tocopherol; or,
   d. sialic acid.

4. A method of irrigating or flushing body tissue during surgical procedures which comprises bringing the composition of claim 1 into contact with said tissue.

5. A method of irrigating or flushing body tissue during surgical procedures which comprises bringing the composition of claim 2 into contact with said tissue.

6. A method of irrigating or flushing body tissue during surgical procedures which comprises bringing the composition of claim 3 into contact with said tissue.

* * * * *